United States Patent [19]
Virnig et al.

[11] Patent Number: 5,939,034
[45] Date of Patent: Aug. 17, 1999

[54] PROCESS FOR THE RECOVERY OF PRECIOUS METAL VALUES FROM AQUEOUS AMMONIACAL THIOSULFATE LEACH SOLUTIONS

[75] Inventors: Michael J. Virnig; J. Michael Sierakoski, both of Tucson, Ariz.

[73] Assignee: Henkel Corporation, Gulph Mills, Pa.

[21] Appl. No.: 08/878,263

[22] Filed: Jun. 17, 1997

Related U.S. Application Data

[60] Provisional application No. 60/020,593, Jun. 26, 1996.
[51] Int. Cl.$^6$ .................................................. C22B 11/00
[52] U.S. Cl. ................................. 423/24; 423/32
[58] Field of Search ................... 423/24, 32, 33

[56] References Cited

U.S. PATENT DOCUMENTS

| | | | |
|---|---|---|---|
| 3,920,403 | 11/1975 | Ross | 423/27 |
| 4,070,182 | 1/1978 | Genik-Sas-Berezowsky et al. | 75/103 |
| 4,563,256 | 1/1986 | Sudderth et al. | 204/108 |
| 4,814,007 | 3/1989 | Lin et al. | 75/118 |
| 4,895,597 | 1/1990 | Lin et al. | 75/118 |
| 4,992,200 | 2/1991 | Lin et al. | 252/184 |
| 5,158,603 | 10/1992 | Stierman et al. | 75/743 |
| 5,340,380 | 8/1994 | Virnig | 75/744 |
| 5,354,359 | 10/1994 | Wan et al. | 75/744 |
| 5,536,297 | 7/1996 | Marchbank et al. | 75/736 |

FOREIGN PATENT DOCUMENTS

| | | | |
|---|---|---|---|
| 937288 | 9/1993 | South Africa . | |
| 91/11539 | 8/1991 | WIPO | 423/24 |

OTHER PUBLICATIONS

"The Basic Strength of Methylated Guanidines", S. J. Angyal and W. K. Worberton, pp. 2492–2494 of J. Chem. Soc., 1951.
International Search Report for PCT/US97/08654 mailed Aug. 29, 1997.

*Primary Examiner*—Steven Bos
*Attorney, Agent, or Firm*—Ernest J. Szoke; Wayne C. Jaeschke; Patrick J. Span

[57] ABSTRACT

The process of recovering precious metals from ores containing precious metals, such as gold and silver, from an aqueous ammoniacal thiosulfate leach solution to provide a significant practical and economical process for the recovery of gold or silver is disclosed. After leaching of the ore with an aqueous ammoniacal thiosulfate solution, the leach solution is contacted with a precious metal extraction reagent to extract the precious metal values from the leach solution, after which the precious metal values are stripped from the extraction reagent to form a concentrated solution of the precious metal values from which the precious metals may be recovered by conventional methods such as electrolysis. The extraction reagents are those having guanidyl functionality or a quaternary amine functionality mixed with a weak organic acid such as a phenol.

In the process, novel thiosulfate complexes of the precious metals are formed with the quanidyl or the quaternary amine extractants.

22 Claims, No Drawings

PROCESS FOR THE RECOVERY OF PRECIOUS METAL VALUES FROM AQUEOUS AMMONIACAL THIOSULFATE LEACH SOLUTIONS

CROSS-REFERENCE TO RELATED APPLICATIONS

This application claims priority from U.S. provisional application Ser. No. 60/020,593, filed Jun. 26, 1996, the disclosure of which is incorporated herein by reference.

FIELD OF THE INVENTION

This invention relates to the recovery of precious metals, such as gold and silver, from aqueous ammoniacal thiosulfate leach solutions by extraction of the precious metal values from the aqueous thiosulfate leach solution with organic amine extractants, such as guanidine compounds or mixtures of a quaternary amine and a phenol.

Conventionally, precious metals have been leached from ore using cyanide containing solutions and the precious metals recovered therefrom. However, other metals present tend to cause problems in the process of recovery of the precious metals. One method proposed for overcoming the problems involved the use of extractant reagents to remove the precious metals from the aqueous cyanide containing solution, either by liquid/liquid extraction or by liquid/solid extraction systems.

More recently a South African patent application, Serial No. 937288 to Newmont Gold Co. (Newmont Mining Corporation) was published relating to a process of recovering precious metals from ores employing a thiosulfate lixiviant as leach solution from which the precious metals are recovered from the lixiviant leach solution by means other than extraction technology, preferably by precipitation and cementation techniques.

No fully satisfactory process has been developed however, for precious metals recovery from ore materials containing other base metals which interfere with or render the process of recovery of the precious metals non-viable from a practical or commercial standpoint.

SUMMARY OF THE INVENTION

It has now been found that by leaching the gold containing ore with an aqueous ammoniacal thiosulfate solution and extracting the metal values therefrom, a viable, practical process is provided, affording a simple means for avoiding the problem arising from the presence of other metals present with the precious metals in the aqueous ammoniacal thiosulfate leach solution provided, but also providing for the recovery of the precious metal, particularly gold, in a purer form than that provided by other techniques.

Briefly, in its broadest scope, one aspect of the present invention is a process for recovering precious metals, particularly gold and silver, from ores containing the precious metals and other base metals, comprising:

(a) providing an aqueous ammoniacal thiosulfate leach solution containing the precious metal values and other base metal values contained in the ore;

(b) contacting the aqueous ammoniacal thiosulfate leach solution from step (a) with a metal value extraction reagent for a time sufficient to extract precious metal values from the aqueous ammoniacal thiosulfate leach solution;

(c) stripping the precious metal values from the extraction reagent; and (d) recovering the precious metal values from the aqueous stripping solution.

Extraction step (b) is carried out by either a liquid/liquid solvent extraction or by a liquid/solid extraction technique employing an extraction reagent capable of extracting precious metal values from aqueous solutions. In a liquid/liquid solvent extraction system, a water insoluble extraction reagent capable of forming a complex with the metals to be extracted is dissolved in a water-immiscible organic hydrocarbon solvent. In the solid/liquid extraction system, the extractant reagent is one incorporated and/or chemically bonded onto a solid ion exchange resin matrix or carrier or backbone. Both of these extraction systems will be discussed in more detail hereafter.

The extraction reagents for use in the present invention to be described in more detail hereafter are (i) guanidine compounds employed as hydrocarbon solvent solution in the liquid/liquid extraction system or chemically bonded to a resin matrix or backbone to provide an ion exchange resin carrying guanidyl functionality and (ii) a reagent comprising a mixture of a quaternary amine and a weak organic acid, such as a phenol, which reagent may be employed in the same manner as the guanidine reagent, in the liquid/liquid solvent extraction system.

A second aspect of the invention is the provision of precious metal (gold or silver) ammonium thiosulfate complexes of the extractant reagents employed, guanidyl or quaternary amine complexes.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The aqueous ammoniacal thiosulfate leach solution is provided by contacting a body of particles or particulates of precious metal ore material containing the precious metals with a thiosulfate lixiviant under conditions providing for intimate contact of the two. The body of particles or particulates may comprise a heap of particles and particulates and contacting the heap by passing the thiosulfate solution through the heap by applying it to the heap at a flow rate under conditions which cause the solution to flow through the heap and intimately wet the ore particle. The thiosulfate solution containing precious metal values, such as gold or silver, is recovered at the bottom of the heap. With higher grade ore materials containing greater amounts of precious metals may be processed by forming a slurry of the thiosulfate solution and finely ground ore in a stirred vessel.

The thiosulfate leach solution or lixiviant can derive the necessary thiosulfate ion from a variety of sources of thiosulfate, such as ammonium thiosulfate or alkali metal or alkaline earth metal thiosulfates, such as sodium or potassium, which are preferred, or calcium thiosulfate. The thiosulfate leach system preferably has (a) an ammonium thiosulfate or sodium thiosulfate (or mixture of both) concentration of at least about 0.025M of ammonium thiosulfate corresponding to about 4 grams of ammonium thiosulfate per liter of leach solution preferably from about 0.05M to about 0.2M (corresponding to about 7.5 to about 30 grams of ammonium thiosulfate per liter of leach solution). (b) The aqueous leach solution will preferably have a pH of about 8 to about 10, and more preferably about 9 to about 9.5, and an ammonia concentration in an amount sufficient to stabilize the thiosulfate complex, generally at least about 0.05M preferably at least about 0.1M.

As earlier briefly noted, in a liquid/liquid extraction method, the reagent must be soluble in an organic solvent which is immiscible in relation to the aqueous ammoniacal thiosulfate leach solution. Thus, the guanidine reagent is dissolved in the organic solvent, which is then brought in contact with the aqueous cyanide solution containing the desired metal values. The guanidine reagent extracts the gold and/or silver metals from the thiosulfate leach solution which are now found in the organic phase which is immiscible with the aqueous phase. After separation of the organic phase from the aqueous phase, the organic phase containing the desired metal values is then stripped by contact with an aqueous caustic solution which strips the metal values from the organic phase. It may be desireable to add a small amount of cyanide to the aqueous caustic strip solution to maintain the precious metals in solution, especially silver. The metal values now in a more concentrated aqueous solution are then recovered by conventional methods such as those used in the carbon absorption method through eletrowinning.

In the liquid/solid extraction method, a guanidine reagent is first incorporated into a solid ion exchange carrier. Recovery of the gold from the thiosulfate solution is accomplished by contacting the thiosulfate solution with the ion exchange reagent carrier containing the guanidine functionality, at which point the metals are extracted from the aqueous thiosulfate solution onto the ion exchange carrier containing the guanidine reagent. The metal barren aqueous solution is then separated from the carrier containing the guanidine. The metal values are then stripped from the ion exchange carrier containing the guanidine functionality and recovered in the same manner as in the liquid/liquid extraction method.

Accordingly, the present invention is directed to a process for the recovery of precious metals, such as gold or silver, from an aqueous ammoniacal thiosulfate solution containing such metal values comprising (1) contacting the aqueous solution with a compound containing a functional guanidine group to extract at least a portion of the precious metal values from the aqueous solution (2) separating the resultant metal-barren solution from the guanidine compound, and (3) recovering the precious metals from the guanidine compound.

By guanidine functionality is meant those compounds, reagents or ion exchange resins containing the functional group:

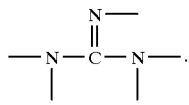

In regard to the ion exchange resins the group is bonded by chemical reaction to the resin through any one of the N atoms. The remaining bonds of the nitrogen atom are filled by hydrogen, aliphatic or aromatic hydrocarbon groups or cyclic (including heterocyclic groups containing nitrogen atoms), straight or branched chain, saturated and unsaturated, as will be discussed in more detail in the description to follow. Aspects and advantages of the present invention will be apparent to those skilled in the art upon consideration of the following detailed description thereof.

The liquid/liquid process of the invention is a liquid ion exchange process in which a water-insoluble guanidine compound is dissolved in an essentially water-immiscible liquid hydrocarbon solvent and the resulting solution is contacted with a metal-containing aqueous phase to extract a portion of the metal values into the organic phase. The phases are then separated and metal values are stripped from the organic phase by the use of an aqueous stripping medium.

A wide variety of essentially water-immiscible liquid hydrocarbon solvents can be used in the metal recovery process of the present invention. These include: aliphatic and aromatic hydrocarbons such as kerosenes, high flashpoint ($\geq 150°$ F.) petroleum distillates, benzene, toluene, xylene and the like. A choice of the essentially water-immiscible liquid hydrocarbon solvents for particular commercial operations will depend on a number of factors, including the design of the solvent extraction plant (i.e. mixer-settler units, Podbielniak extractors, etc.), the value of the metal being recovered, and the like. The process of the present invention finds particular use in the extraction recovery of the precious metals, such as gold and/or silver. The preferred solvents for use in these precious metal recovery processes of the present invention are the aliphatic and aromatic hydrocarbons having flash points of 150° F. and higher and solubilities in water of less than 0.1% by weight. The solvents are also essentially chemically inert. Representative commercially available solvents are Kermac 470B (an aliphatic kerosene available from Kerr-McGee-flash point 175° F.), Chevron ion exchange solvent (available from Standard Oil of California-flash point 195° F.), Escaid 100 and 110 (available from Exxon-Europe-flash point 180° F.), Norpar 12 (available from Exxon-USE-flash point 160° F.), Conoco-C1214 (available from Conoco-flash point 60° F., Aromatic 150 (an aromatic kerosene available from Exxon-USA-flash point 150° F.), the various other kerosenes and petroleum fractions available from other oil companies. In the process of the present invention, the organic solvent solutions will preferably contain from about 0.02 to 20% by weight of the guanidine compound and even more preferably from about 0.1–5% by weight thereof. Additionally, volume ratios of the organic:aqueous phase vary widely since the contacting of any quantity of the guanidine solution with the metal containing aqueous phase will result in extraction of metal values into the organic phase. However, for commercial practicality, the organic:aqueous phase ratios are preferably in the range of about 50:1 to 1:50. It is desirable to maintain an effective 0 to A ratio of about 1:1 in the mixer in a continuous circuit by recycle of one of the streams. For practical purposes the extracting and stripping are normally conducted at ambient temperatures and pressures, although higher and/or lower temperatures and/or pressures are entirely operable. Most advantageously, the entire process can be carried out continuously with the stripped organic solvent solution being recycled for contacting further quantities of the precious metal-containing thiosulfate solutions. As indicated, in a liquid/liquid extraction process the guanidine reagent must be soluble in the organic water-immiscible solvent to the extent of about 0.02% by weight, or capable of being soluble to such extent through the use of a solubility modifier substance. Such solubility modifiers suitable for use n the present invention include long chain ($C_6$–$C_{20}$)aliphatic alcohols such as n-hexanol, 2-ethylhexanol, isodecanol, dodecanol, tridecanol, hexadecanol and octadecanol; long chain alkyl phenols such as heptylphenol, octylphenol, nonylphenol and docecylphenol; and organo-phosphorus compounds such as tri-lower alkyl ($C_4$–$C_8$) phosphates, especially tributyl phosphate and tri(2-ethylhexyl) phosphate.

The extraction of the precious metals from their aqueous solution depends on a number of factors including, for example, the concentration of the metal ion, the particular anions present and the pH of the aqueous solutions and the concentration of and the particular guanidine used in the organic phase. Thus, for each aqueous metal solution and reagent solution of guanidine, there will be a preferred or optimum set of extraction conditions and those skilled in the art based on the information given herein, will be able with a limited number of trial runs to determine such preferred or optimum conditions for the specific system under consideration. This is equally true of the stripping operations. By stripping is meant that at least a portion of the metal values in the loaded organic phase are transferred to the aqueous stripping medium. The metal values are then desirably recovered from the aqueous stripping medium by conventional techniques, preferably electrolysis. The loaded organic:aqueous stripping phase ratios can also vary widely. However, the overall object of the process is to provide a metal containing stripping solution of known composition and concentration suitable for the conventional recovery techniques such as by electrolysis. Thus, normally the metal will preferably be present in higher concentrations in the aqueous stripping medium than in the starting metal-containing solution. In this regard the starting aqueous metal-containing solutions will contain from about 0.5 to 5 ppm of gold and 0.5 to 100 ppm of silver along with copper plus other metals. A heap leach liquor will average 0.5 to 2 ppm gold, 0.5 to 20 ppm silver and along with copper plus other metals. The concentrations of gold in the aqueous strip solutions from which the gold will be recovered will be anywhere from about 5 to 1000 ppm. This will largely depend on the stripping solutions employed and the efficiency thereof. In the stripping step, the loaded organic:aqueous stripping medium phase ratio will preferably be in the range of about 1:1 to 20:1. The aqueous stripping solutions for use in the present invention will generally be basic stripping solutions having pH in excess of 11.0. The stripping reagent preferably employed is caustic sodium hydroxide solution having a pH above 11, generally 12 or above. After removal of the metal from the aqueous stripping solution by conventional techniques, the caustic aqueous solution in a continuous circuit is recycled.

The foregoing description has dealt with the liquid/liquid extraction systems. As earlier indicated, liquid/solid systems can be employed, in which a guanidine reagent is incorporated into an ion exchange resin by chemically bonding the guanidine functionality to the resin backbone. In this regard, the term "extracting" used herein is to be understood as including both liquid and solid means for selectively removing and otherwise separating the precious metal values. As the ion exchange resin containing the guanidine functionality will be used to treat or contact a precious metals containing aqueous solution, the ion exchange resin must be one which is water-insoluble. Upon contact of the aqueous thiosulfate solution containing the precious metals, the precious metals are selectively absorbed by the guanidine reagent on the ion exchange resin. The metal values are then eluted from the ion exchange resin by contact with the sodium hydroxide solution such as the stripping solution mentioned earlier above. With the liquid/solid system, it may be desireable to add cyanide to the strip solution along with an alkali metal salt of an aliphatic or aromatic carboxylic acid having from 4 to 14 carbon atoms, preferably sodium benzoate. The techniques employed in the production of water-insoluble ion exchange resins employed in the process of the present invention are well-known to those skilled in the art, and especially, to those skilled in the art of polymerizing monomers to produce polymeric compositions useful as ion exchange resins. Examples of the preparation of resin carriers for the extraction reagents of the present invention can be found in Henkel Corporation U.S. Pat. Nos. 5,340,380 and 5,156,603. In the present invention, the preferred ion exchange resin is a chloromethylated polystyrene, which upon chemical reaction with the appropriate compound, provides a guanidine functionality carried by the ion exchange resin. One of the preferred ion exchange resins useful in the present invention is chloromethylated polystyrene, 1.06 meq chloride/g, 2% divinylbenzene (DVB). The particle size of the ion exchange resin can vary widely, so long as the size range is generally fine enough to exhibit desirable loading and elution kinetics and yet large enough to (a) allow solution to flow through the bed without binding or building up excess pressure: and (b) allow convenient screening of the resin from the aqueous solution. Preferably, about a #32 mesh size (0.5 mm opening) is employed. The loading of the water-insoluble ion exchange resins with the guanidine can vary widely. Generally, it will be determined by the bed-volume characteristics of the particular water-insoluble ion exchange resin. Typically, the flow rates through the ion exchange bed will be such as to assure effective absorption onto the water-insoluble ion exchange resins.

After the water-insoluble ion exchange resin containing the guanidine reagent has been loaded with the precious metal values, the aqueous thiosulfate solution is separated from the ion exchange resin and the absorbed precious metal values are eluted from the ion exchange resin. The suitable eluents as indicated are the same as earlier described. The most efficient and effective eluent is an aqueous solution of sodium hydroxide having a pH above 11.

As indicated, both the liquid/liquid and liquid/solid extraction processes require reagents containing a guanidine functional group which may ideally be defined as:

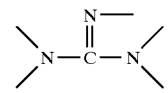

For use in the liquid/liquid extraction process these are water-insoluble guanidine compounds which are soluble in water immiscible hydrocarbon solvents, and where precious metal salts are soluble therein, to the extent of at least 0.22% by weight. For use in the extraction process the compounds also have a pKa of greater than 12 and preferably than 13. A discussion of basic strengths of methylated guanidine and pKa values thereof can be seen in "The Basic Strength of Methylated Guanidines", S. J. Angyal and W. K. Worberton, pages 2492–2494 of J. Chem. Soc., 1951. Examples of the preparation of a variety of guanidine compounds can be seen from Henkel Corporation U.S. Pat. Nos. 4,992,200 and 4,895,597. In the liquid/solid extraction process, an ion exchange resin incorporates the guanidine functionality by chemical reaction with the guanidine compounds. Thus, the guanidine reagent suitable for use in the present extraction processes may be further illustrated by means of the idealized formula:

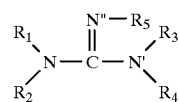

wherein $R_1$ through $R_5$ is selected from the group consisting of H, an ion exchange resin backbone and aromatic and aliphatic groups having up to 25 carbon atoms. Preferably, as noted earlier, guanidine compounds which are extraction reagents in the liquid/liquid system or which are chemically reacted with the ion exchange resin from the liquid/solid system are those having a pKa at 25° C. greater than 12. Aromatic groups such as phenyl, tend to decrease the basicity to a level below a pKa of 12 and accordingly it is preferred that not more than one of the R groups should be phenyl. The ion exchange resin may be bonded to the guanidine to any one of the nitrogen atoms such as at N" or N or N'.

With regard to the guanidine functionality reagents, the preferred reagent for the liquid/liquid extraction system is N,N'-bis(cyclohexyl)-N"-isotridecyl guanidine. For the liquid/solid extraction system, the preferred reagent is unsubstituted guanidine itself carried by a styrene, divinyl benzene resin matrix or carrier in which the guanidine is attached to the benzene ring of the resin through a $CH_2$ group resulting from chloromethylation of the polystyrene.

As noted earlier, another extraction reagent is a quaternary amine mixed with a weak organic acid. By "weak organic acid" is meant herein a water insoluble organic compound which will provide an acidic proton and have a $pK_a$ as measured in water in the range of about 8–12. The weak organic acid provides a pH dependent counterion thereby providing a means of controlling the pH behavior of the quaternary amine to extract the desired metal complex anion from the aqueous, ammoniacal thiosulfate solution.

The quaternary amines which can be used in the process according to the invention are those having the formula II

$$R_6R_7R_8R_9N^+X^-  \qquad \text{II}$$

wherein $X^-$ is an anion, each of $R_6$, $R_7$, $R_8$, and $R_9$ is a hydrocarbon radical containing up to 25 carbon atoms, and wherein the sum of carbon atoms in the total of $R_6$, $R_7$, $R_8$, and $R_9$ is at least 16. Preferably at least one of $R_6$, $R_7$, $R_8$, and $R_9$ groups will have at least 6 carbon atoms and no more than two of $R_6$, $R_7$, $R_8$, and $R_9$ groups will be methyl. The preferred quaternary amine is one in which three of $R_6$, $R_7$, $R_8$, and $R_9$ groups are alkyl groups having at least 6 carbon atoms, such as tri($C_8$–$C_{10}$)methyl ammonium chloride, available from Henkel Corporation as Aliquat® 336. The preferred weak organic acids for use with the quaternary amine extractant, which can be used in the process according to the invention are alkyl phenols having the formula III and IV

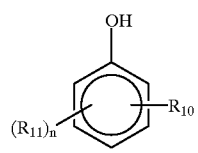

(III)

(IV)

wherein $R_{10}$ is hydrogen or an electron-withdrawing group selected from the group consisting of Cl, Br,

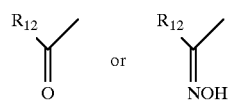

wherein $R_{12}$ is hydrogen or a hydrocarbon radical having from 1 to 25 carbon atoms with the proviso that the total number of carbon atoms in $R_{11}$ and $R_{12}$ is from 6 to 30; n is an integer from 0 to 4; and $R_{11}$ is an alkyl group having from 1 to 25 carbon atoms, preferably from 7 to 12 carbon atoms. The preferred phenols are heptylphenol, octylphenol, nonylphenol, and dodecylphenol, for use with the preferred quaternary amine (Aliquat® 336).

Where metals other than gold and silver are extracted with the ammoniacal thiosulfate leach solution, such as copper and zinc, such metal values, which may be present as an ammonium complex, and may be selectively extracted from the aqueous solution either before or after the extraction of the precious metal values as discussed above. These metals may be selectively removed by extraction with reagent selective to such metals, which are well known and recognized by those skilled in the art. For example, selective extraction of copper and zinc metals may be carried out by the use of aryl hydroxy oximes, aldoximes or ketoximes, as described in Henkel Corporation U.S. Pat. No. 4,563,256. Other metals may be selectively extracted in similar fashion employing extractants known for extraction for the specific metal to be removed.

Alternatively, in liquid/solid systems, the guanidine functionalized resin can be replaced by solid supports such as styrene-divinylbenzene resin beads, urethane foams or activated carbon particles impregnated with an organic phase containing an alkylguanidine or a mixture of the quaternary amine and an alkylphenol.

The invention may be further illustrated by the following examples of the invention.

EXAMPLE 1

A gold and/or silver bearing ore is contacted with an ammoniacal thiosulfate solution containing low levels of copper as the cupric tetramine complex for a sufficient period of time to maximize recovery of the precious metal values. The ammoniacal thiosulfate lixiviant solution is prepared in such a manner that it will contain from 7.5 to 30 grams per liter of ammonium thiosulfate; an ammonia concentration, preferably at least 0.05M and more preferably at least 0.1M, sufficient to stabilize the thiosulfate complexes of the precious metals and the cupric tetramine complex; sufficient cupric tetramine (20–60 ppm of Cu) to catalyse the oxidation of the gold, and a pH of at least about 9 and preferably between about 9.2 and 10. Optionally, the lixiviant solution may contain some sulfite in addition to the thiosulfate. The ore is contacted with the lixiviant solution by a number of possible processes including a column, vat leach, agitated vat leach, or by applying the lixiviant solution to the ore in a heap or pad leach.

The pregnant leach solution containing the precious metal values is then separated from the spent ore and transferred to extraction where it is contacted with an organic phase consisting of an alkylguanidine such as N,N'-bis(cyclohexyl)-N"-isotridecylguanidine or a quaternary amine, Aliquat 336, in combination with an alkylphenol, nonyl or dodecylphenol, dissolved in a typical hydrocarbon diluent, such as, Conoco 170E, Phillips Orfom SX-7. In the case of the alkylguanidine, the organic phase may also contain an amount of a branched chain alcohol such as isotridecyl alcohol (Exaal 13 available from Exxon) sufficient (0–100 gram per liter; more preferably 10–100 gpl) to keep the extracted precious metal thiosulfate complexes soluble in the organic phase. When using the quaternary amine/alkylphenol mixture, the molar ratio of quaternary amine to alkylphenol is in the range from 1:1 to 1:3 with the most preferred range being between 1:1.5 to 1:2.5. The organic phase is typically from 0.001M to 0.04M in either the alkylguanidine or the quaternary amine. The extractant concentration is adjusted to obtain the desired recoveries of the precious metal thiosulfate complexes. After contacting the pregnant leach solution with organic phase, the loaded organic phase containing the precious metals is separated from the aqueous raffinate phase and transferred to stripping where the loaded organic is contacted with an aqueous caustic solution consisting of typically from 0.1 to 1M and most preferably from 0.25M to 1M sodium hydroxide along with sufficient sodium cyanide to maintain the precious metals in solution. The stripped organic is regenerated in this process and returned to extraction for refuse. The pregnant aqueous strip solution is then transferred to a metal recovery process where the precious metal values are recovered by electrowinning or by cementation with a metal such as zinc, copper, or aluminum.

Alternatively, the pregnant leach solution can be passed through a column containing a resin functionalized with a guanidine (Aurix®resin) to recover the precious metal values. The precious metal values are then removed from the loaded resin by contacting the resin with an aqueous caustic solution containing sufficient sodium cyanide to maintain the precious metals in solution as well as an effective amount of sodium benzoate to promote stripping.

The concentration of ammonia, thiosulfate and cupric tetramine complex is adjusted in the aqueous raffinate from extraction and returned as lixiviant to leaching.

EXAMPLE 2

Finely ground ore containing gold and/or silver values is agitated with the ammonium thiosulfate lixiviant solution described in Example 1 to form a pulp, a guanidine functionalized resin (Aurix®resin) is added to the pulp, and the mixture is agitated for a sufficient period of time to effect reasonable recoveries of the precious metal values. The loaded resin is then separated from the pulp, typically by screening and transferred to elution where it is loaded into a column. The loaded resin is then eluted as described in Example 1 and then returned to extraction.

What is claimed is:

1. A process for the recovery of precious metals from an aqueous ammoniacal thiosulfate leach solution containing the precious metals comprising:
    (a) contacting the aqueous ammoniacal thiosulfate leach solution containing the precious metals values with a precious metal extraction reagent for a time sufficient to extract or remove the precious metal values from the leach solution;
    (b) stripping the precious metal values from the precious metal extraction reagent with an aqueous stripping solution; and
    (c) recovering the precious metal from the aqueous stripping solution;
in which the precious metal extraction reagent in step (a) is selected from the group consisting of (i) one having a guanidyl functionality and (ii) a quaternary amine mixed with a weak organic acid.

2. A process as defined in claim 1, wherein the precious metal is gold or silver.

3. A process as defined in claim 1, wherein the extraction reagent in step (a) is one having guanidyl functionality.

4. A process as defined in claim 3 wherein the extraction reagent having guanidyl functionality has the formula

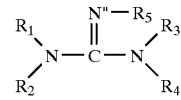

wherein $R_1$ through $R_5$ is selected from the group consisting of H, an ion exchange resin carrier and hydrocarbon groups having up to 25 carbon atoms and provided further that when one of the R groups $R_1$ through $R_5$ is an ion exchange resin carrier, the remaining R groups are H or an aliphatic or aromatic hydrocarbon group having up to 25 carbon atoms.

5. A process as defined in claim 4 wherein when one of the R groups $R_1$ through $R_5$ is an ion exchange resin carrier to which the guanidine functionality is chemically bonded to the carrier, the remaining R groups are all hydrogen providing an unsubstituted guanidyl functionality.

6. A process as defined in claim 4 wherein the extraction reagent having guanidyl functionality is a water insoluble guanidine compound soluble in a water-immiscible hydrocarbon solvent and having a pKa value at 25° C. greater than 10.

7. A process as defined in claim 6 wherein the pKa value is greater than 12.

8. A process as defined in claim 6 wherein the guanidine compound is N,N'-bis(cyclohexyl)-N"-isotridecyl guanidine.

9. A process as defined in claim 6 wherein said hydrocarbon solvent is kerosene or a petroleum distillate fraction having a flash point of 150° F. or higher.

10. A process as defined in claim 6, wherein, on contacting the aqueous ammoniacal thiosulfate solution with the water-immiscible organic hydrocarbon solvent solution of the water-insoluble guanidine compound, thereby extracting the precious metal values from the aqueous, thiosulfate solution into the organic water-immiscible organic hydrocarbon solvent solution and two phases form a water-immiscible organic phase, now containing the precious metal values and an aqueous phase from which the precious metal values have been removed, and separating the two phases.

11. A process as defined in claim 10 wherein the organic phase, is contacted with a caustic solution having a pH above 11 thereby stripping the precious metal values from the organic phase and providing an aqueous strip solution now containing the precious metal values in a more concentrated form than the original leach solution.

12. A process as defined in claim 11 wherein the aqueous strip solution is separated from the organic phase from which the precious metal values have been stripped.

13. A process as defined in claim 12, wherein the precious metals are removed by electrolysis of the aqueous strip solution.

14. A process as defined in claim 11 wherein the aqueous caustic stripping solution is a NaOH or KOH solution.

15. A process as defined in claim 1, wherein the extraction reagent in step (a) is a quaternary amine mixed with a weak organic acid.

16. A process as defined in claim 15 wherein the quaternary amine has the formula

wherein X⁻ is an anion, each of $R_6$, $R_7$, $R_8$ and $R_9$ is a hydrocarbon radical containing up to 25 carbon atoms, and wherein the sum of carbon atoms in the total of $R_6$, $R_7$, $R_8$ and $R_9$ is at least 16.

17. A process as defined in claim 16 wherein at least one of the $R_6$, $R_7$, $R_8$ and $R_9$ groups will have at least 6 carbon atoms and no more than two of the $R_6$, $R_7$, $R_8$ and $R_9$ groups will be methyl.

18. A process as defined in claim 16 wherein three of the $R_6$, $R_7$, $R_8$ and $R_9$ groups are alkyl groups having at least 6 carbon atoms.

19. A process as defined in claim 16, wherein the quaternary amine is tri ($C_8$–$C_{10}$) methyl ammonium chloride.

20. A process as defined in claim 15 wherein the weak organic acid is an alkyl phenol having the formula III or IV

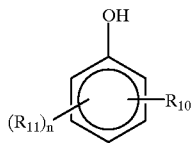
(III)

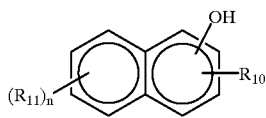
(IV)

wherein $R_{10}$ is hydrogen or an electron-withdrawing group selected from the group consisting of Cl, Br,

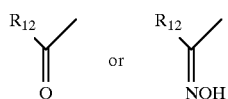

wherein $R_{12}$ is hydrogen or a hydrocarbon radical having from 1 to 25 carbon atoms with the proviso that the total number of carbon atoms in $R_{11}$ and $R_{12}$ is from 6 to 30; n is an integer from 0 to 4; and $R_{11}$ is an alkyl group having from 1 to 25 carbon atoms, preferably from 7 to 12 carbon atoms.

21. A process as defined in claim 15, wherein the quaternary amine is tri ($C_8$–$C_{10}$) methyl ammonium chloride and the phenol is selected from the group consisting of heptylphenol, octylphenol, nonylphenol and dodecylphenol.

22. A process for the recovery of precious metals from an aqueous thiosulfate solution containing the precious metals comprising:

(a) contacting the aqueous thiosulfate solution containing the precious metal values with a precious metal extraction reagent selected from the group consisting of (i) one having a guanidyl functionality and (ii) a quaternary amine mixed with a weak organic acid for a time to form a thiosulfate complex with the extraction reagent thereby extracting or removing the precious metal values from the aqueous thiosulfate solution;

(b) stripping the precious metal values from the extraction reagent with an aqueous caustic stripping solution; and (c) recovering the precious metal from the aqueous stripping solution.

* * * * *